(12) United States Patent
Spero et al.

(10) Patent No.: US 11,465,146 B2
(45) Date of Patent: Oct. 11, 2022

(54) SMALL VOLUME SAMPLE COLLECTION DEVICE AND RELATED SYSTEMS AND METHODS

(71) Applicants: Redbud Labs, Inc., Research Triangle Park, NC (US); THE UNIVERSITY OF NORTH CAROLINA AT THE CHAPEL HILL, Chapel Hill, NC (US)

(72) Inventors: Richard Chasen Spero, Chapel Hill, NC (US); Jay Kenneth Fisher, Durham, NC (US); Richard Superfine, Chapel Hill, NC (US)

(73) Assignees: Redbud Labs, Inc., Research Triangle Park, NC (US); The University of North Carolina at Chapel Hill, Chapel Hill, NC (US)

( * ) Notice: Subject to any disclaimer, the term of this patent is extended or adjusted under 35 U.S.C. 154(b) by 189 days.

(21) Appl. No.: 16/347,729

(22) PCT Filed: Nov. 17, 2017

(86) PCT No.: PCT/US2017/062359
§ 371 (c)(1),
(2) Date: May 6, 2019

(87) PCT Pub. No.: WO2018/094245
PCT Pub. Date: May 24, 2018

(65) Prior Publication Data
US 2019/0307383 A1 Oct. 10, 2019

Related U.S. Application Data

(60) Provisional application No. 62/424,352, filed on Nov. 18, 2016.

(51) Int. Cl.
*B01L 3/00* (2006.01)
*A61B 5/15* (2006.01)
(Continued)

(52) U.S. Cl.
CPC ........ *B01L 3/502746* (2013.01); *A61B 5/153* (2013.01); *A61B 5/150022* (2013.01);
(Continued)

(58) Field of Classification Search
CPC .. B01L 3/502746; B01L 3/5027; B01L 3/502; B01L 3/50; A61B 5/150022;
(Continued)

(56) References Cited

U.S. PATENT DOCUMENTS 2,237,213 A 4/1941 Brown
5,174,162 A 12/1992 Miyake et al.
(Continued)

*Primary Examiner* — Christine T Mui
(74) *Attorney, Agent, or Firm* — E. Eric Mills; Nexsen Pruet, PLLC

(57) ABSTRACT

A system, mixing-enhanced microfluidic container, and methods for small volume sample collection and/or analysis is disclosed. Namely, the invention is directed to a small volume sample collection system that includes a mixing-enhanced microfluidic container and a durable reusable actuation chuck. The mixing-enhanced microfluidic container is used to collect small volumes of sample fluid and includes a means for mixing the sample fluid with reagents disposed within the microfluidic container. The mixing means utilize an array of surface-attached structures (e.g., a micropost array). The application of an "actuation force," such as a magnetic or electric field, actuates the surface-attached structures into movement, wherein the actuation chuck in close proximity to the mixing-enhanced microfluidic container provides the "actuation force."

21 Claims, 17 Drawing Sheets

(51) Int. Cl.
*A61B 5/153* (2006.01)
*A61B 5/151* (2006.01)
*A61B 5/157* (2006.01)
*G01N 1/38* (2006.01)
*B01L 3/02* (2006.01)
*B01F 33/81* (2022.01)
*B01F 33/30* (2022.01)

(52) U.S. Cl.
CPC .. *A61B 5/150343* (2013.01); *A61B 5/150755* (2013.01); *B01L 3/502715* (2013.01); *A61B 5/15003* (2013.01); *A61B 5/157* (2013.01); *A61B 5/15142* (2013.01); *B01F 33/3038* (2022.01); *B01F 33/813* (2022.01); *B01L 3/0275* (2013.01); *B01L 2200/027* (2013.01); *B01L 2200/0647* (2013.01); *B01L 2200/0684* (2013.01); *B01L 2200/16* (2013.01); *B01L 2400/084* (2013.01); *B01L 2400/086* (2013.01); *G01N 1/38* (2013.01)

(58) Field of Classification Search
CPC ................ A61B 5/150007; A61B 5/15; A61B 5/150343; A61B 5/150755
USPC .......................................... 422/509, 500, 50
See application file for complete search history.

(56) References Cited

U.S. PATENT DOCUMENTS

| | | | |
|---|---|---|---|
| 5,443,791 | A | 8/1995 | Cathcart et al. |
| 8,586,368 | B2 * | 11/2013 | Superfine ............... G01N 11/16 436/69 |
| 9,080,207 | B2 * | 7/2015 | Handique ............ C12Q 1/6806 |
| 2003/0039589 | A1 * | 2/2003 | Smith ................... B01L 3/0275 422/513 |
| 2009/0004063 | A1 | 1/2009 | Higashihara et al. |
| 2010/0291615 | A1 | 11/2010 | Ronsick et al. |
| 2012/0101407 | A1 | 4/2012 | Chan |
| 2013/0280143 | A1 | 10/2013 | Zucchelli et al. |
| 2016/0195457 | A1 | 7/2016 | Black |

* cited by examiner

SMALL VOLUME SAMPLE COLLECTION DEVICE AND RELATED SYSTEMS AND METHODS

CROSS-REFERENCE TO RELATED APPLICATIONS

The present application is a 371 national phase entry of international application PCT/US2017/062359, filed Nov. 17, 2017, which claims priority to provisional patent application No. 62/424,352 filed Nov. 18, 2016, which are incorporated herein by reference in their entireties.

TECHNICAL FIELD OF THE INVENTION

The presently disclosed subject matter relates generally to methods of collecting and analyzing biological fluids (or biofluids) and more particularly to a system, mixing-enhanced microfluidic container, and methods for small volume sample collection and/or analysis.

BACKGROUND

Currently, there are two scenarios of blood collection and analysis—(1) blood collection and analysis in a high resource environment, and (2) blood collection and analysis in a low resource environment. There are limitations to both the high and low resource environments.

An example of the high resource environment of blood collection and analysis is the hospital environment. In a hospital environment, large volumes (e.g., 1-10 ml) of blood can be collected via, for example, a central line or venipuncture and collected into a vacutainer. Then, the vacutainer of blood sample is sent to a central laboratory and processed (i.e., analyzed) using, for example, a robot and multi-well microplate. One problem of the high resource environment of blood collection and analysis is that the blood volume draws are much larger than they need to be. A severe example of this problem is neonates. There might be only 10 ml of blood in the baby and collecting 1 ml of this blood is problematic. Often, babies are transfused, just to do the diagnostics.

An example of the low resource environment of blood collection and analysis is the near patient point-of-care (POC) environment. For example, a fingerstick or other small volume draw (e.g., 5-500 µL) can be collected in a capillary tube or on a test strip. Then, analysis can be performed on a small mobile diagnostic device. However, the quality of the blood from a fingerstick is poor compared to a large volume venous blood draw. For example, when skin is punctured with a lancet, skin cells and other impurities are released into the blood sample droplet. Further, a small volume of blood in a capillary tube does not stabilize quickly and shaking a capillary tube does not induce mixing. Therefore, when blood from the capillary tube, which is not a homogeneous mixture, is placed on a dried reagent surface in the diagnostic device, the reagent rehydrates unevenly, micro-clots can be present, and so on.

SUMMARY OF THE INVENTION

A small volume sample collection system is provided, comprising:
 a mixing-enhanced microfluidic container configured to collect a sample comprising a volume of biological fluid of less than about 0.1 ml; and
 a reusable actuation chuck;
 wherein the mixing-enhanced microfluidic container comprises a reaction chamber, wherein the reaction chamber further comprises reagents disposed within the reaction chamber and mixing means configured to mix the biological fluid with the reagents.

In some embodiments, the mixing means comprise an array of surface-attached structures configured for actuation in the presence of an actuation force. In other embodiments, the reusable actuation chuck is configured to provide the actuation force when the mixing-enhanced microfluidic container is contacted with the actuation chuck. In other embodiments, the mixing-enhanced microfluidic container is installed within the reusable actuation chuck. In other embodiments, the actuation force is selected from the group consisting of a magnetic field, a thermal field, a sonic field, an optical field, an electrical field, and a vibrational field.

In other embodiments, the reagents disposed within the reaction chamber are disposed on or integrated with the inside surface of the reaction chamber. In other embodiments, the reagents disposed within the reaction chamber are disposed on or integrated with the outer surface of at least some of the surface-attached structures.

In other embodiments, the biological fluid is selected from the group consisting of blood, urine, saliva, sputum, mucus, feces, tumor fluid, needle biopsy fluid, peritoneal fluid, cerebral spinal fluid, tears, sweat, synovial fluid, semen, ear fluid, breast milk, and bile. In other embodiments, the biological fluid is blood, and the mixing-enhanced microfluidic container is configured to collect blood samples produced via lancet or via central line.

In other embodiments, the mixing-enhanced microfluidic container is configured to connect to a point-of-care (POC) diagnostic device. In other embodiments, the mixing-enhanced microfluidic container is configured to connect to a dispensing pipette.

In other embodiments, the small volume sample collection system further comprises a plurality of mixing-enhanced microfluidic containers and reusable actuation chucks, wherein the plurality of mixing-enhanced microfluidic containers are configured to connect to a plurality of dispensing pipettes configured in an array for high-throughput sample processing.

In other embodiments, the reaction chamber is configured to hold from about 5 µL to about 500 µL of sample fluid. In other embodiments, the reaction chamber is configured to hold about 50 µL of sample fluid.

In other embodiments, a fluid port supplies one end of the reaction chamber and a vent mechanism is provided at the other end of the reaction chamber. In other embodiments, a central line is mechanically and fluidly coupled to the fluid port. In other embodiments, a cap is mechanically coupled to the vent mechanism.

In other embodiments, the reusable actuation chuck comprises a housing, wherein the housing comprises a wraparound portion for receiving the fluid port end of the mixing-enhanced microfluidic container. In other embodiments, the wraparound portion comprises a slot configured to allow the central line to pass through the slot. In other embodiments, the housing comprises a cap portion and a holding portion, wherein the cap portion is configured to engage with the cap end of the mixing-enhanced microfluidic container, and wherein the holding portion is arranged between the wraparound portion and the cap portion of the housing. In other embodiments, the holding portion is configured to hold the reaction chamber. In other embodiments, the actuation chuck further comprises one or more components selected from the group consisting of a battery, a motor, one or more magnets, a pump, a controller, one or more visual, audible, and/or tactile indicators, and a communications interface.

In other embodiments, the fluid port comprises a nozzle. In other embodiments, the fluid port is configured for both drawing sample fluid and dispensing sample fluid. In other embodiments, the fluid port is a female type of coupler for snap-fitting onto a fitting at the end of the central line. In other embodiments, the fitting comprises a split septum or leur lock fitting. In other embodiments, the vent mechanism comprises a vapor seal. In other embodiments, the vent mechanism comprises a seal that is gas permeable but not liquid permeable. In other embodiments, the vent mechanism comprises a silicone seal. In other embodiments, the vent mechanism is configured to facilitate a pumping action within the reaction chamber via the application of positive pressure and negative pressure to the vent mechanism. In other embodiments, an end of the cap is coupled to the vent mechanism and an opposite end of the cap is coupled to a pumping mechanism. In other embodiments, a channel is provided through the cap by which air can escape from the vent mechanism. In other embodiments, the cap comprises a split septum.

In other embodiments, the reaction chamber comprises a first sidewall and a second sidewall separated by a gap; the array of surface-attached structures are attached to a substrate on the first sidewall facing the gap; and a dried reagent surface is provided on the second sidewall facing the gap; wherein the gap is filled with the volume of biological fluid. In other embodiments, the first and second sidewalls are substantially optically transparent. In other embodiments, the surface-attached structures are chemically inert. In other embodiments, the surface-attached structures are functionalized with analyte capture elements.

In other embodiments, the surface-attached structures are microposts. In other embodiments, the microposts are formed of polydimethylsiloxane (PDMS). In other embodiments, the microposts range in length from about 1 μm to about 100 μm. In other embodiments, the microposts range in diameter from about 0.1 μm to about 10 μm. In other embodiments, the microposts have a cross-sectional shape selected from the group consisting of circular, ovular, square, rectangular, and triangular. In other embodiments, the microposts are oriented substantially normal to the plane of the substrate. In other embodiments, the microposts are oriented at an angle α with respect to normal of the plane of the substrate. In other embodiments, the microposts are oriented at a pitch of from about 0 μm to about 50 μm.

A high-throughput sample processing system is also provided comprising:
  a plurality of mixing-enhanced microfluidic containers, wherein each of the mixing-enhanced microfluidic containers:
    is configured to collect a sample comprising a volume of biological fluid of less than about 0.1 ml;
    is installed within an actuation chuck;
    comprises a cap; and
    comprises a reaction chamber, wherein the reaction chamber further comprises reagents disposed within the reaction chamber and mixing means configured to mix the biological fluid with the reagents;
  a multiwell microplate; and
  a robot comprising a plurality of pipette adaptor tips, wherein each of the pipette adaptor tips is configured to receive the cap and apply positive pressure for dispensing the biological fluid.

In some embodiments, the mixing means comprise an array of surface-attached structures configured for actuation in the presence of an actuation force. In other embodiments, the reagents disposed within the reaction chamber are disposed on or integrated with the inside surface of the reaction chamber and/or are disposed on or integrated with the outer surface of at least some of the surface-attached structures. In other embodiments, the reaction chamber is configured to hold from about 5 μL to about 500 μL of sample fluid. In other embodiments, the reaction chamber is configured to hold about 50 μL of sample fluid. In other embodiments, a fluid port supplies one end of the reaction chamber and a vent mechanism is provided at the other end of the reaction chamber. In other embodiments, the actuation chuck further comprises one or more components selected from the group consisting of a battery, a motor, one or more magnets, a pump, a controller, one or more visual, audible, and/or tactile indicators, and a communications interface.

In other embodiments, a small volume sample collection system is provided, comprising;
  a mixing-enhanced microfluidic container configured to collect a sample comprising
  a volume of biological fluid of less than about 0.1 ml; and
  an actuation subsystem integrated together with the mixing-enhanced microfluidic container;
wherein the mixing-enhanced microfluidic container comprises a reaction chamber, wherein the reaction chamber further comprises reagents disposed within the reaction chamber and mixing means configured to mix the biological fluid with the reagents. In some embodiments, the mixing means comprise an array of surface-attached structures configured for actuation in the presence of an actuation force. In other embodiments, the actuation subsystem comprises a mechanism that generates an actuation force with respect to the array of surface-attached structures. In other embodiments, the actuation force is selected from the group consisting of magnetic, thermal, sonic, optical, electrical, and vibrational. In other embodiments, the actuation subsystem comprises a motor and magnets. In other embodiments, the mixing-enhanced microfluidic container is disposable. In other embodiments, the mixing-enhanced microfluidic container is integrated with the actuation mechanism via a printed circuit board, a thin film magnetic circuit, or wires embedded in the mixing means.

In a further embodiment, in either the reusable actuation chuck or the integrated magnet configuration, the actuator is a permanent magnet configured such that shaking the device causes the magnet and therefore the microposts to move.

Methods of using the presently disclosed small volume sample collection system are also provided. In some embodiments, methods are provided for using the presently disclosed small volume sample collection system with an indwelling line in a high resource environment such as a hospital setting, without drawing an excess of sample fluid, i.e., more than is needed. Methods are also provided for using the presently disclosed small volume sample collection system with a point-of-care (POC) device in a low resource environment of blood collection and analysis.

BRIEF DESCRIPTION OF THE DRAWINGS

The features and advantages of the present invention will be more clearly understood from the following description taken in conjunction with the accompanying drawings, which are not necessarily drawn to scale, and wherein.

DETAILED DESCRIPTION OF EXEMPLARY EMBODIMENTS

Figure 1:
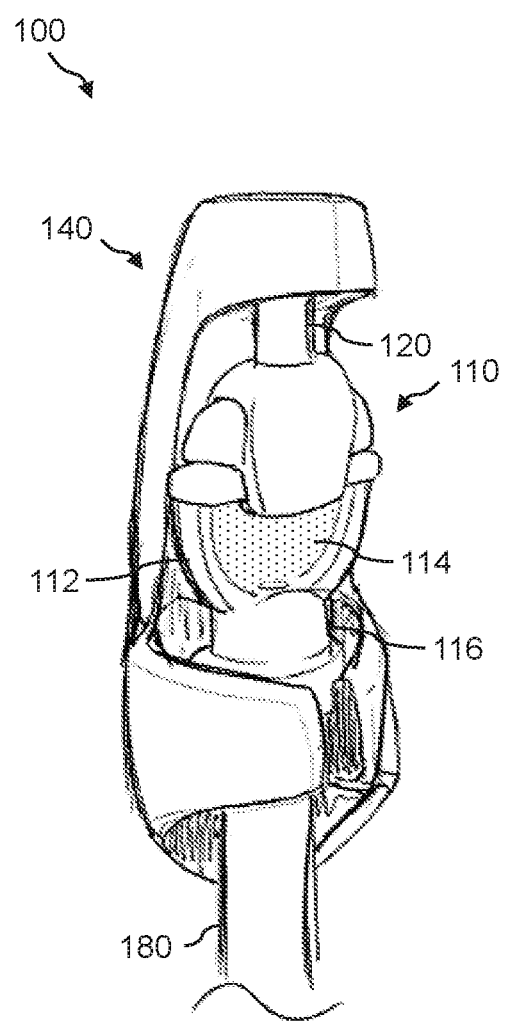
FIG. 1 illustrates a perspective view of an example of the presently disclosed small volume sample collection system that includes a mixing-enhanced microfluidic container and a reusable actuation chuck.

In some embodiments, the presently disclosed subject matter provides a system, mixing-enhanced microfluidic container, and methods for small volume sample collection and/or analysis. Namely, the invention is directed to a small volume sample collection system that includes a mixing-enhanced microfluidic container and a durable reusable actuation chuck.

The mixing-enhanced microfluidic container is a small volume sample collection device for processing any type of biological fluid (or biofluid). For example, the mixing-enhanced microfluidic container is used to collect small volumes of blood (e.g., blood droplets, volumes of less than about 0.1 ml) and includes a means for mixing the blood samples with reagents disposed within the microfluidic container. The mixing means utilize an array of surface-attached structures (e.g., a micropost array). The application of a magnetic or electric field actuates the surface-attached structures into movement. For example, the actuation occurs by contacting the mixing-enhanced microfluidic container with the actuation chuck comprising elements that provide an "actuation force," such as a magnetic or electric field.

In the mixing-enhanced microfluidic container of the presently disclosed small volume sample collection system, the reagents may be disposed on or integrated with the outer surface of at least some of the surface-attached structures, or disposed on or integrated with the inside surface of the device, or both of the foregoing.

Further, in the presently disclosed small volume sample collection system, the mixing-enhanced microfluidic container may be configured to collect blood samples produced via lancet or via central line. The mixing-enhanced microfluidic container also may be configured to connect to point-of-care (POC) diagnostic devices or to dispensing pipettes. Dispensing pipettes can in turn be configured in arrays for high-throughput sample processing.

An aspect of the presently disclosed small volume sample collection system that includes a mixing-enhanced microfluidic container and an actuation chuck is that it is useful in both the high and low resource environments of blood collection and analysis. Namely, the mixing-enhanced microfluidic container is useful for both collection and analysis and can be integrated with any type of existing collection and analysis infrastructure.

Another aspect of the presently disclosed small volume sample collection system that includes a mixing-enhanced microfluidic container and an actuation chuck is that the mixing-enhanced microfluidic container provides enhanced mixing in a capillary draw device that is not currently possible in, for example, POC low resource environments.

Yet another aspect of the presently disclosed small volume sample collection system that includes a mixing-enhanced microfluidic container and an actuation chuck is that the mixing-enhanced microfluidic container can be configured for sample fluid collection, sample fluid analysis, or both sample fluid collection and analysis.

Figure 2A:
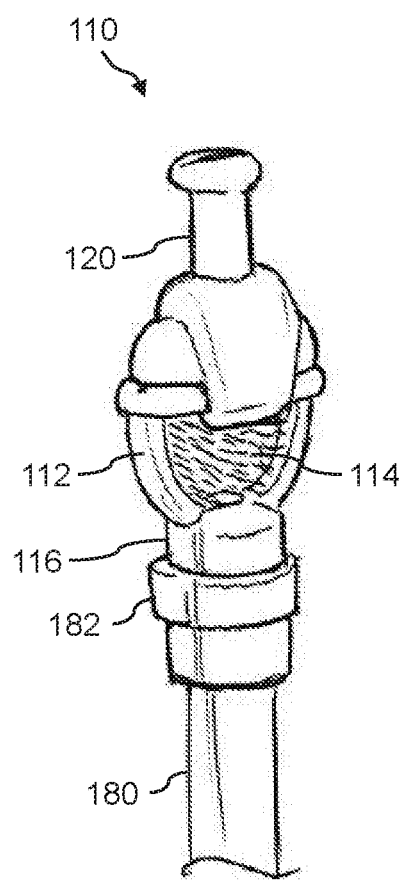
FIG. 2A illustrates a perspective view of the mixing-enhanced microfluidic container of the small volume sample collection system shown in FIG. 1.
Figure 2B:
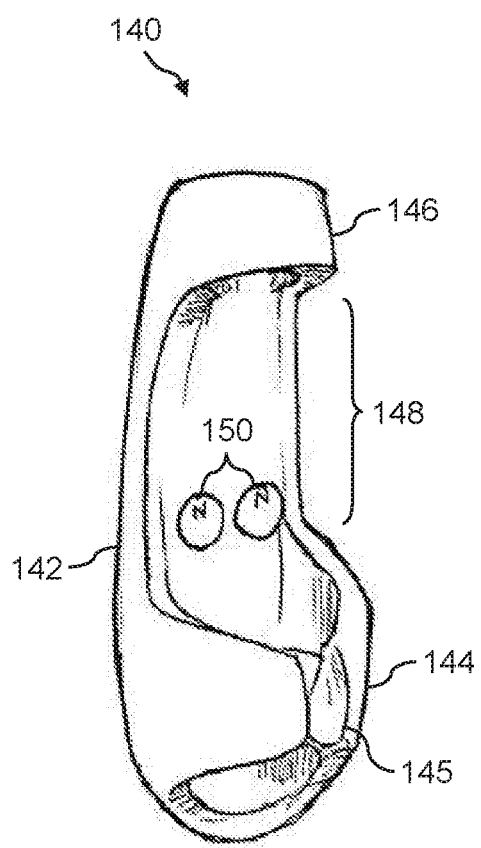
FIG. 2B illustrates a perspective view of the reusable actuation chuck of the small volume sample collection system shown in FIG. 1.

FIG. 1 illustrates a perspective view of an example of the presently disclosed small volume sample collection system 100 that includes a mixing-enhanced microfluidic container 110 and an actuation chuck 140. While FIG. 1 shows mixing-enhanced microfluidic container 110 installed in actuation chuck 140, FIG. 2A and FIG. 2B show mixing-enhanced microfluidic container 110 and actuation chuck 140 separately.

Mixing-enhanced microfluidic container 110 includes a reaction chamber 112. Reaction chamber 112 provides a space or void in mixing-enhanced microfluidic container 110 for holding a small volume of sample fluid. Processing and/or analysis of a sample fluid may be performed within reaction chamber 112. In one example, reaction chamber 112 can be sized to hold from about 5 μL to about 500 μL of sample fluid. In another example, reaction chamber 112 is sized to hold about 50 μL of sample fluid.

An array of microposts 114 are arranged inside reaction chamber 112. A fluid port 116 supplies one end of reaction chamber 112 and a vent mechanism (see FIG. 3) is provided at the other end of reaction chamber 112. A cap 120 is mechanically coupled to the vent mechanism of reaction chamber 112. In this example, a central line 180 (e.g., plastic tubing) is mechanically and fluidly coupled to fluid port 116 of reaction chamber 112. More details of mixing-enhanced microfluidic container 110 are shown and described hereinbelow with reference to FIG. 3 and FIG. 7.

Actuation chuck 140 is a reusable durable chuck. Actuation chuck 140 includes a housing 142, which has a wraparound or shroud or cocoon or shell type of shape. Namely, housing 142 has a wraparound portion 144 for receiving the fluid port 116-end of mixing-enhanced microfluidic container 110. Wraparound portion 144 has a slot 145 through which, for example, central line 180 may pass. Housing 142 also has a cap portion 146 for engaging with the cap 120-end of mixing-enhanced microfluidic container 110. Further, a holding portion 148 is arranged between wraparound portion 144 and cap portion 146 of housing 142. Holding portion 148 that is sized and shaped to hold the reaction chamber 112-portion of mixing-enhanced microfluidic container 110. FIG. 2B also shows that actuation chuck 140 includes magnets 150, wherein magnets 150 can provide the actuation force for microposts 114 inside reaction chamber 112 of mixing-enhanced microfluidic container 110. Other components of actuation chuck 140 are integrated into housing 142. Example components include, but are not limited to, a battery; a motor; magnets 150; a pump; a microcontroller; visual, audible, and/or tactile indicators; and the like. More details of actuation chuck 140 are shown and described hereinbelow with reference to FIG. 7.

Figure 3:
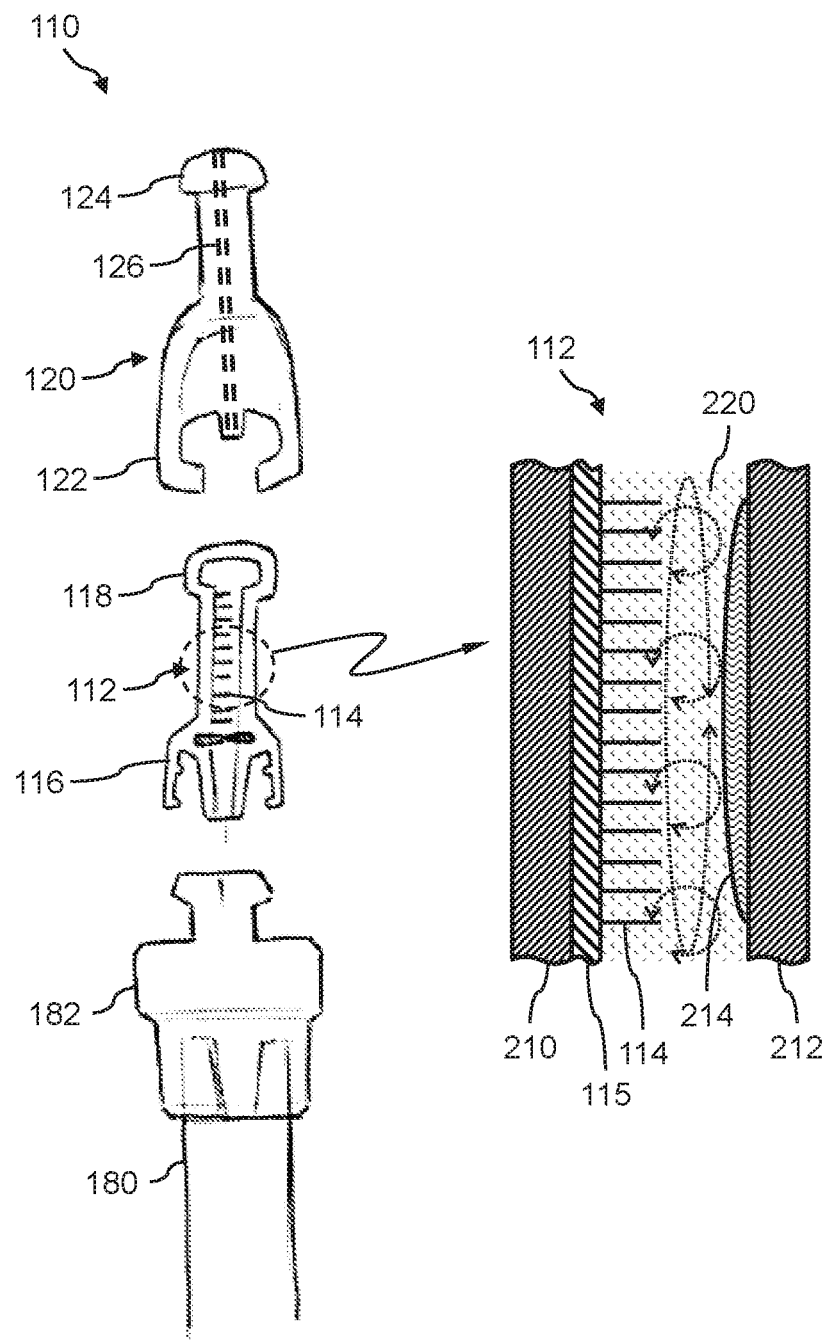
FIG. 3 illustrates an exploded side view of the mixing-enhanced microfluidic container shown in FIG. 1 and FIG. 2A.

FIG. 3 illustrates an exploded side view of mixing-enhanced microfluidic container 110 shown in FIG. 1 and FIG. 2A. Namely, FIG. 3 shows reaction chamber 112 with the array of microposts 114 arranged inside, fluid port 116 at one end of reaction chamber 112, and a vent mechanism 118 at the other end of reaction chamber 112. Fluid port 116 is a nozzle for both drawing sample fluid, such as blood, into reaction chamber 112 and dispensing sample fluid from reaction chamber 112. Fluid port 116 can be implemented in any number of ways depending on the type of collection/analysis system to which it will be coupled. That is, fluid port 116 can be implemented one way for one type of collection/analysis system and another way of another type of collection/analysis system. In the example shown in FIG. 3, fluid port 116 is a female type of coupler for snap-fitting onto a fitting 182 at the end of central line 180 (e.g., plastic tubing). Fitting 182 can be, for example, a split septum or leur lock fitting used in, for example, a hospital environment. Other types of fluid ports 116 are shown and described hereinbelow with reference to FIG. 8A and FIG. 8B.

Vent mechanism 118 is a vapor seal at the end of reaction chamber 112 opposite fluid port 116. Namely, vent mechanism 118 is a seal that is gas permeable but not liquid permeable. That is, vent mechanism 118 allows gas (e.g., air) to pass through but does not allow liquid (e.g., biofluid) to pass through. Vent mechanism 118 can be, for example, a silicone seal. In one example, vent mechanism 118 allows air to vent out of reaction chamber 112 while blood is loading. At the same time, vent mechanism 118 blocks blood from exiting when reaction chamber 112 is full.

Further, because vent mechanism 118 is a seal that is gas permeable but not liquid permeable, vent mechanism 118 can be used to facilitate pumping action within reaction chamber 112 of mixing-enhanced microfluidic container 110. In one example, positive pressure can be applied to vent mechanism 118 for dispensing sample fluid from mixing-enhanced microfluidic container 110. In another example, negative pressure (i.e., vacuum) can be applied to vent mechanism 118 for drawing sample fluid into mixing-enhanced microfluidic container 110. Accordingly, cap 120 is a hard cap that can be bonded to vent mechanism 118 and provides a fluid path in contact with vent mechanism 118. For example, an end 122 of cap 120 is designed to couple to vent mechanism 118. An opposite end 124 of cap 120 is designed to couple to a pumping mechanism (not shown). A channel 126 is provided through cap 120 by which air can escape from vent mechanism 118 of reaction chamber 112. In one example, end 124 of cap 120 has a split septum design.

Referring still to FIG. 3, a magnified view of reaction chamber 112 shows more details thereof. For example, reaction chamber 112 includes a first sidewall (or substrate) 210 and a second sidewall (or substrate) 212 that are separated by a gap. The array of microposts 114 are arranged on a substrate 115 that is arranged on the side of sidewall 210 facing the gap. A layer or dots of dried reagent 214 is on the side of sidewall 212 facing the gap for form a dried reagent surface. The gap is filled with a volume of sample fluid 220. Sample fluid 220 can be any type of biofluid to be processed. Examples of biofluids that can be processed in mixing-enhanced microfluidic container 110 include, but are not limited to, urine, saliva, sputum, mucus (e.g., cervicovaginal mucus, nasal mucus), feces, tumor fluid, needle biopsy fluid, peritoneal fluid, cerebral spinal fluid, tears, sweat, synovial, semen, ear fluid, breast milk, bile, and the like.

The components of reaction chamber 112 can be formed, for example, of molded plastic or glass. In some cases, the molded plastic or glass in the area of sidewalls 210, 212 can be substantially optically transparent. For example, to allow both collection and analysis to take place in mixing-enhanced microfluidic container 110, sidewall 212, which is opposite microposts 114, can be substantially transparent so that the sample fluid therein can be analyzed via, for example, optical spectroscopy.

Referring again to FIG. 1, FIG. 2A, FIG. 2B, and FIG. 3, microposts 114 are surface-attached posts wherein each micropost 114 includes a proximal end attached to substrate 115 and a distal end that extends into the gap of reaction chamber 112. Accordingly, the distal ends of microposts 114 extend into sample fluid 220. In one example, microposts 114 are chemically inert and will not react with target analytes in sample fluid 220. However, in another example, the surfaces of the microposts 114 can be functionalized with analyte capture elements.

Microposts 114 are designed to exhibit motion when in the presence of an actuation force. As used herein, the term "actuation force" refers to any force applied to microposts 114 that can cause them to move. Actuation chuck 140 is used to generate an actuation force in proximity to microposts 114 that compels at least some of microposts 114 to exhibit motion. The actuation force may be, for example, magnetic, thermal, sonic, optical, electrical, and/or vibrational. Further, the actuation force may be applied as a function of frequency or amplitude, or as an impulse force (i.e., a step function). Similarly, other actuation forces may be used without departing from the scope of the presently disclosed subject matter, such as fluid flow across microposts 114.

By actuating microposts 114 and causing motion thereof, sample fluid 220 in the gap is in effect stirred or caused to flow or circulate within the gap of reaction chamber 112 and across the surface area of dried reagent 214. Microposts 114 are based on, for example, the microposts described in the U.S. Pat. No. 9,238,869, entitled "Methods and systems for using actuated surface-attached posts for assessing biofluid rheology," issued on Jan. 19, 2016; the entire disclosure of which is incorporated herein by reference. The '869 patent describes methods, systems, and computer readable media for using actuated surface-attached posts for assessing biofluid rheology. According to one aspect, a method of the '869 patent for testing properties of a biofluid specimen includes placing the specimen onto a micropost array having a plurality of microposts extending outwards from a substrate, wherein each micropost includes a proximal end attached to the substrate and a distal end opposite the proximal end, and generating an actuation force in proximity to the micropost array to actuate the microposts, thereby compelling at least some of the microposts to exhibit motion. The method of the '869 patent further includes measuring the motion of at least one of the microposts in response to the actuation force and determining a property of the specimen based on the measured motion of the at least one micropost.

In one example, according to the '869 patent, microposts 114 and substrate 115 can be formed of polydimethylsiloxane (PDMS). Further, microposts 114 may include a flexible body and a metallic component disposed on or in the body, wherein application of a magnetic or electric field actuates microposts 114 into movement relative to the surface to which they are attached. In this example, the actuation force generated by actuation chuck 140 is a magnetic and/or electrical actuation force. More details of microposts 114 are shown and described hereinbelow with reference to FIG. 4A through FIG. 6B.

Figure 4A:
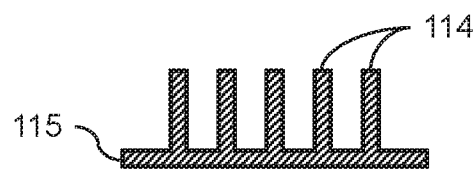
FIG. 4A and FIG. 4B illustrate side views of an example of microposts of the mixing-enhanced microfluidic container.
Figure 4B:
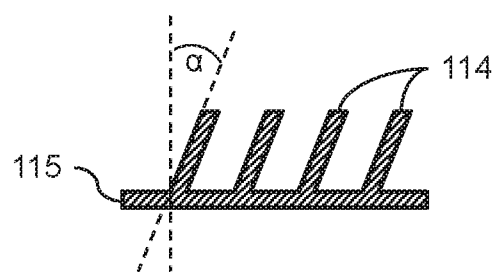

FIG. 4A and FIG. 4B illustrate side views of an example of microposts 114 of mixing-enhanced microfluidic container 110. Again, microposts 114 and substrate 115 can be formed, for example, of PDMS. The length, diameter, geometry, orientation, and pitch of microposts 114 in the array can vary. For example, the length of microposts 114 can vary from about 1 μm to about 100 μm. The diameter of microposts 114 can vary from about 0.1 μm to about 10 μm. The cross-sectional shape of microposts 114 can vary. For example, the cross-sectional shape of microposts 114 can circular, ovular, square, rectangular, triangular, and so on. The orientation of microposts 114 can vary. For example, FIG. 4A shows microposts 114 oriented substantially normal to the plane of substrate 115, while FIG. 4B shows microposts 114 oriented at an angle α with respect to normal of the plane of substrate 115. In a neutral position with no deflection force applied, the angle α can be, for example, from about 0 degrees to about 45 degrees.

Figure 5A:
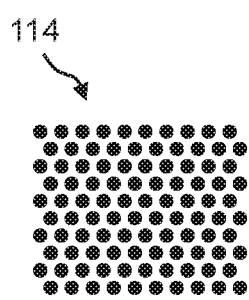
FIG. 5A through FIG. 5E illustrate plan views of examples of configurations of arrays of microposts.
Figure 5B:
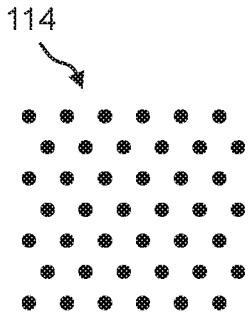
Figure 5C:
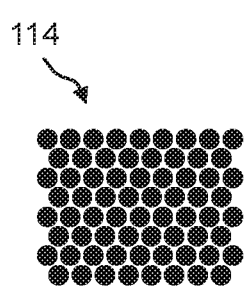
Figure 5D:
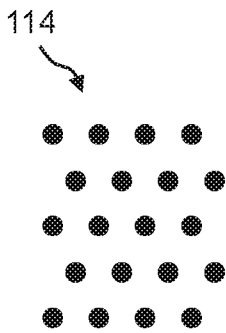
Figure 5E:
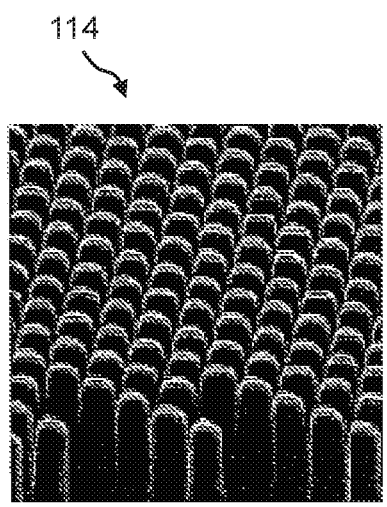

Further, the pitch of microposts 114 within the array can vary, for example, from about 0 μm to about 50 μm. For example, FIG. 5A through FIG. 5D illustrate plan views of examples of configurations of the array of microposts 114. Namely, FIG. 5A shows an example of microposts 114 that are 0.6 μm in diameter and spaced 1.4 μm apart. FIG. 5B shows an example of microposts 114 that are 0.6 μm in diameter and spaced 2.6 μm apart. FIG. 5C shows an example of microposts 114 that are 1 μm in diameter and spaced 1.5 μm apart. FIG. 5D shows an example of microposts 114 that are 1 μm in diameter and spaced 3 μm apart. It is understood that the size and dimensions depicted in FIG. 5A through FIG. 5D are exemplary only and not limiting. FIG. 5E shows a scanning electron microscope image of an example of an array of microposts 114. Further, FIG. 5A through FIG. 5E show the rows of microposts 114 staggered or offset, which is exemplary only.

Figure 6A:
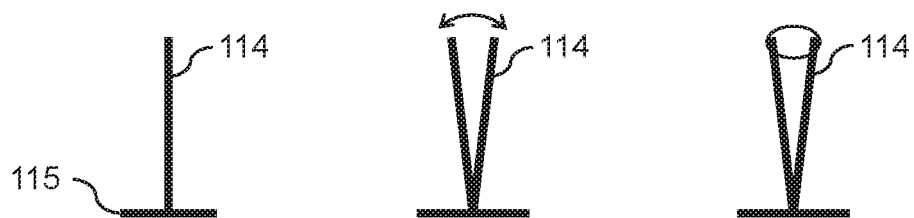
FIG. 6A and FIG. 6B illustrate side views of a micropost and show examples of actuation motion thereof.
Figure 6B:
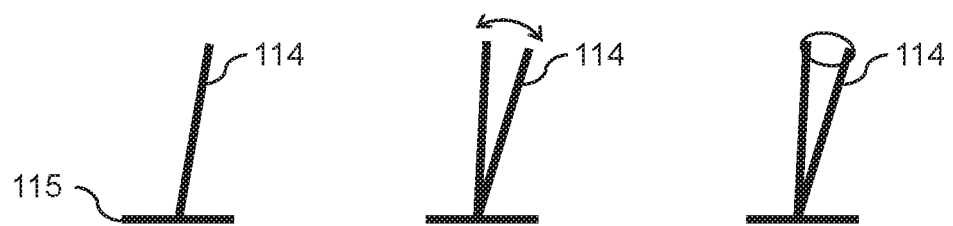

FIG. 6A and FIG. 6B illustrate sides views of a micropost 114 and show examples of actuation motion thereof. Namely, FIG. 6A shows an example of a micropost 114 oriented substantially normal to the plane of substrate 115. FIG. 6A shows that the distal end of the micropost 114 can move (1) with side-to-side 2D motion only with respect to the fixed proximal end or (2) with circular motion with respect to the fixed proximal end, which is a cone-shaped motion. By contrast, FIG. 6B shows an example of a micropost 114 oriented at an angle with respect to the plane of substrate 115. FIG. 6B shows that the distal end of the micropost 114 can move (1) with tilted side-to-side 2D motion only with respect to the fixed proximal end or (2) with tilted circular motion with respect to the fixed proximal end, which is a tilted cone-shaped motion.

Figure 7:
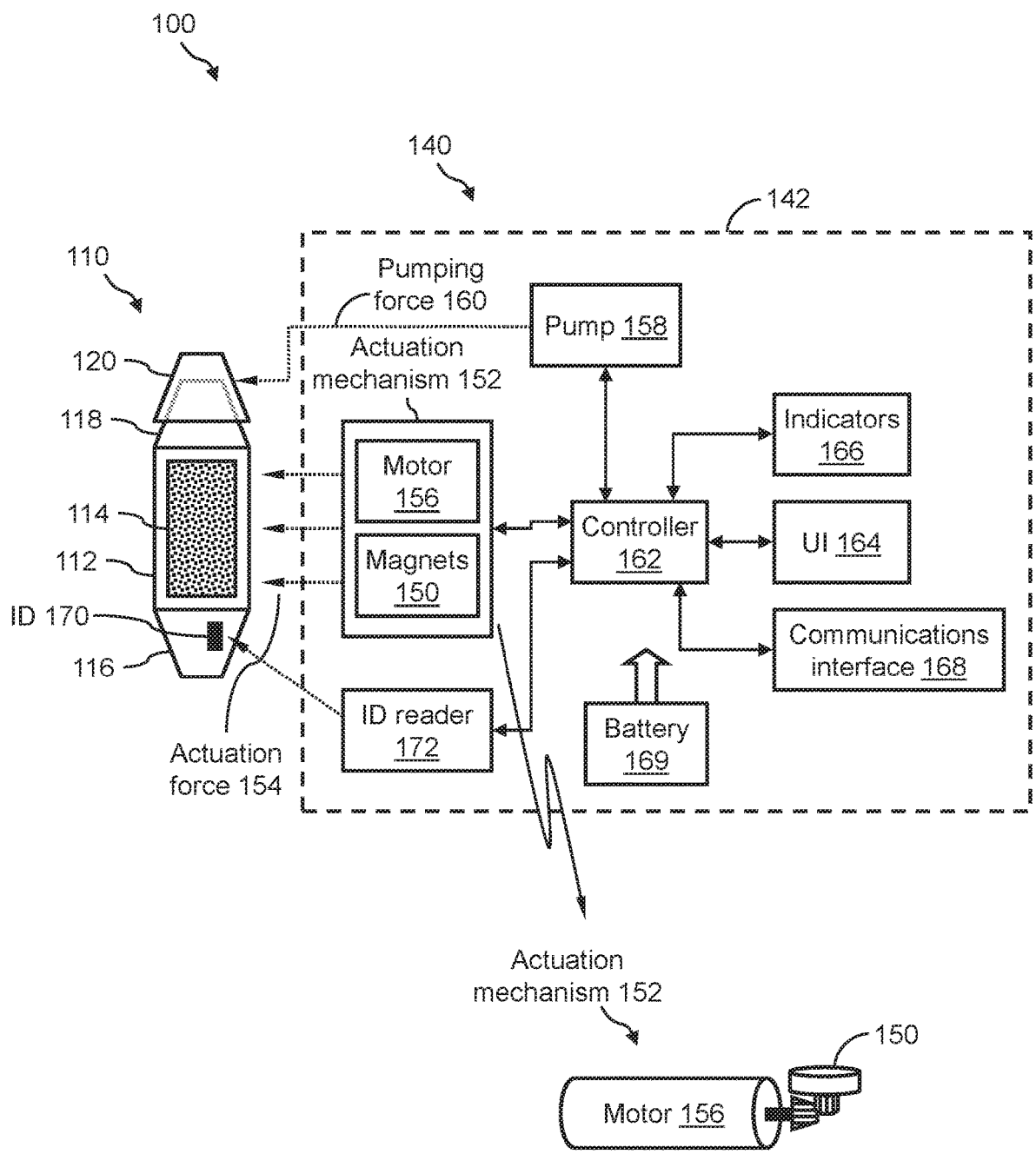
FIG. 7 illustrates a block diagram of the presently disclosed small volume sample collection system that includes a mixing-enhanced microfluidic container and a reusable actuation chuck.

FIG. 7 illustrates a block diagram of the presently disclosed small volume sample collection system 100 that includes mixing-enhanced microfluidic container 110 and actuation chuck 140. As previously disclosed, mixing-enhanced microfluidic container 110 includes reaction chamber 112 that has microposts 114, fluid port 116, vent mechanism 118, and cap 120. Several components are integrated into housing 142 of actuation chuck 140. For example, actuation chuck 140 includes an actuation mechanism 152 that generates an actuation force 154 that is coupled to microposts 114 in mixing-enhanced microfluidic container 110. Actuation mechanism 152 can be any mechanism that generates actuation force 154, wherein actuation force 154 may be, for example, magnetic, thermal, sonic, optical, electrical, and/or vibrational.

In one example, actuation mechanism 152 includes a motor 156 that drives one or more magnets 150, wherein actuation force 154 is a magnetic force. FIG. 2B shows an example of two magnets 150 integrated into housing 142 to be in close proximity to microposts 114 when mixing-enhanced microfluidic container 110 is installed in actuation chuck 140. An example of motor 156 and one magnet 150 is shown in FIG. 7. In this example, a micro-sized cylindrical DC gear motor 156 is geared to a disc permanent magnet 150, wherein the disc permanent magnet 150 can be diametrically magnetized. The micro-sized cylindrical DC gear motor 156 can be, for example, about 6 mm in diameter. The disc permanent magnet 150 can be, for example, about 10 mm in diameter.

Actuation chuck 140 also includes a pump 158 that can deliver a pumping force 160 to vent mechanism 118 of mixing-enhanced microfluidic container 110. Pump 158 can be, for example, a small manual or electric pump (e.g., syringe pump) that can supply positive and/or negative pressure to reaction chamber 112 of mixing-enhanced microfluidic container 110.

Actuation chuck 140 also includes a controller 162. Controller 162 can be any computing device, controller, and/or microcontroller that is capable of executing program instructions. Further, actuation chuck 140 has a user interface (UI) 164 and one or more indicators 166. In one example, UI 164 can include one pushbutton to initiate actuation mechanism 152 and another pushbutton to initiate pump 158. The one or more indicators 166 can include, for example, visual indicators (e.g., light-emitting diodes (LEDs)), audible indicators (e.g., beeps, buzzes), tactile indicators (i.e., vibration), and the like. In one example, upon activation, a green LED (an indicator 166) blinks while the actuation process is in progress and then turns on solid when actuation (i.e., mixing and stabilizing) is complete. In another example, upon activation, short beeping sounds (an indicator 166) are generated while the actuation process is in progress and then the beeps turn to a continuous sound when actuation (i.e., mixing and stabilizing) is complete.

Optionally, actuation chuck 140 can include a communications interface 168. Communications interface 168 can be any wired and/or wireless communication interface for connecting to a network (not shown) and by which information may be exchanged with other devices connected to the network. Examples of wired communication interfaces may include, but are not limited to, USB ports, RS232 connectors, RJ45 connectors, Ethernet, and any combinations thereof. Examples of wireless communication interfaces may include, but are not limited to, an Intranet connection, Internet, ISM, Bluetooth® technology, Bluetooth® Low Energy (BLE) technology, Wi-Fi, Wi-Max, IEEE 402.11 technology, ZigBee technology, Z-Wave technology, 6LoWPAN technology (i.e., IPv6 over Low Power Wireless Area Network (6LoWPAN)), ANT or ANT+ (Advanced Network Tools) technology, radio frequency (RF), Infrared Data Association (IrDA) compatible protocols, Local Area Networks (LAN), Wide Area Networks (WAN), Shared Wireless Access Protocol (SWAP), any combinations thereof, and other types of wireless networking protocols. In one example, communications interface 168 can be used to communicate device health information, such as the battery status.

Additionally, for tracking purposes, each mixing-enhanced microfluidic container 110 can have a unique identification (ID). For example, an ID 170 can be provided on mixing-enhanced microfluidic container 110. ID 170 can be based, for example, on near field communication (NFC) technology, radio frequency identification (RFID) technology, barcode technology, and the like. Therefore, a corresponding ID reader 172 can be integrated into housing 142 of actuation chuck 140. Accordingly, ID reader 172 is also based, for example, on NFC technology, RFID technology, barcode technology, and the like. Using these ID mechanisms, actuation chuck 140 can be used, for example, to track utilization of mixing-enhanced microfluidic containers 110.

In actuation chuck 140, controller 162 can be used to manage the overall operations of actuation chuck 140 including actuation mechanism 152, pump 158, UI 164, indicators 166, communications interface 168, and ID reader 172. Additionally, any information generated by controller 162 can be stored in data storage (not shown), such as any volatile or non-volatile memory device. Further, a battery 169 (e.g., a button battery) supplies power to all active components of actuation chuck 140.

In operation, actuation mechanism 152 generates actuation force 154 in proximity to the array of microposts 114. Actuation force 154 compels at least some of microposts 114 to exhibit motion. In so doing, both regions of local circulation and bulk circulation (see magnified view in FIG. 3) occur within reaction chamber 112 of mixing-enhanced microfluidic container 110. In the presence of the regions of local circulation and bulk circulation, sample fluid 220 can be rapidly mixed and stabilized.

Figures 8A, 8B:
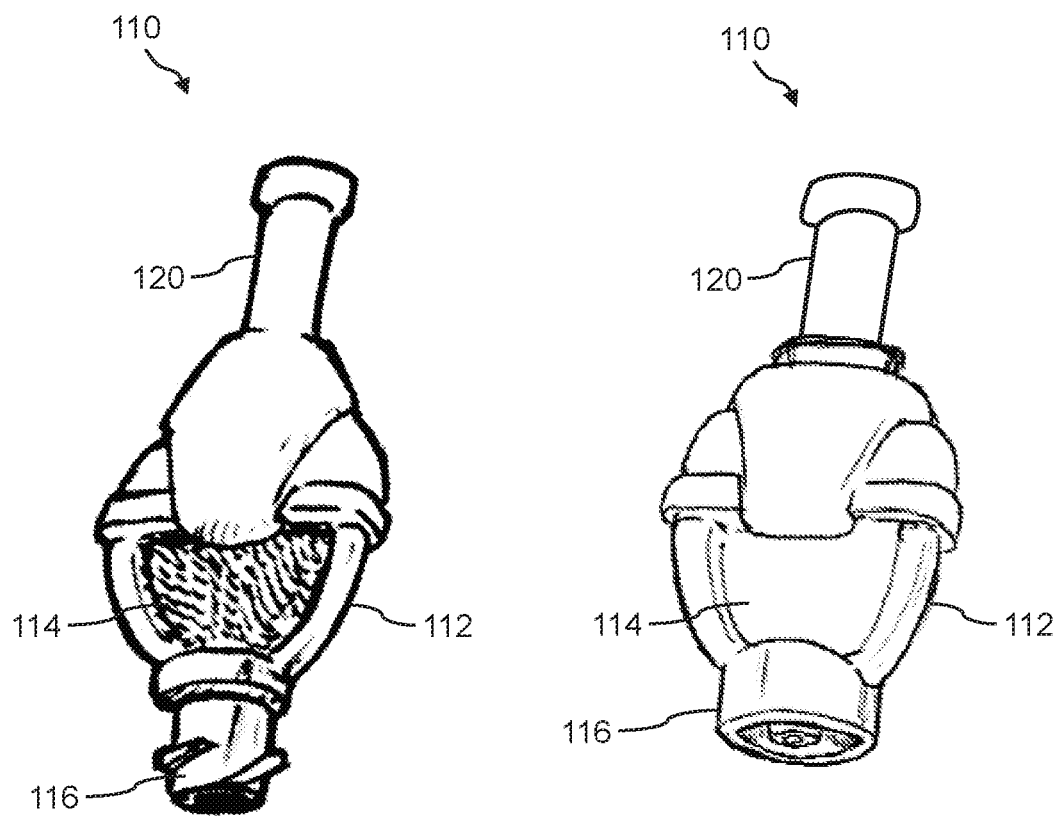
FIG. 8A and FIG. 8B illustrate perspective views of the mixing-enhanced microfluidic container and showing other examples of fluid ports thereof.
Figure 16:
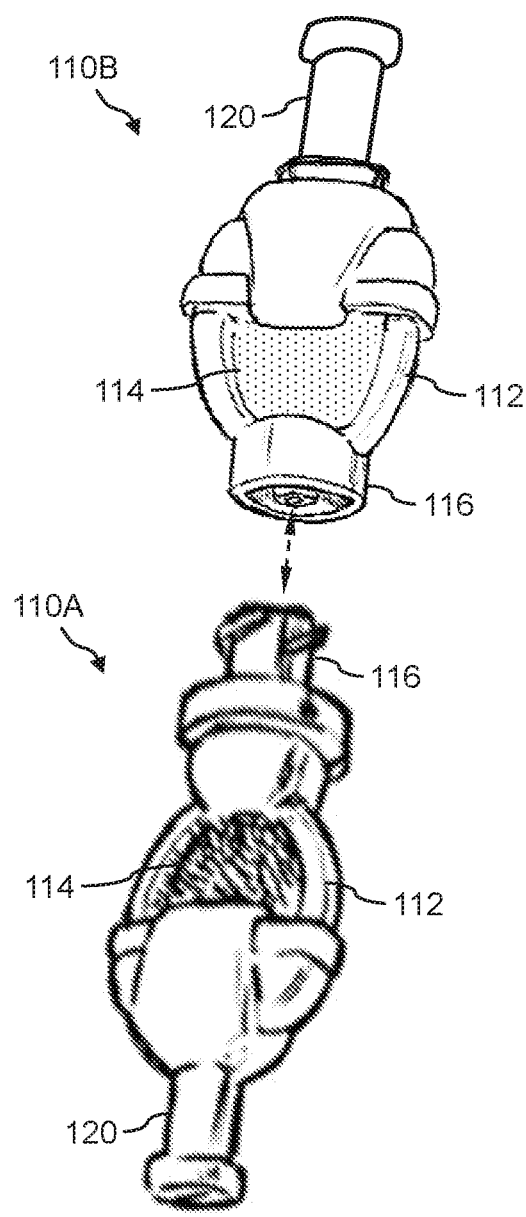
FIG. 16 illustrates an example of a configuration that includes a "collection" mixing-enhanced microfluidic container supplying an "analysis" mixing-enhanced microfluidic container.

FIG. 8A and FIG. 8B illustrate perspective views of mixing-enhanced microfluidic container 110 and showing other examples of fluid ports 116. For example, FIG. 8A shows a threaded male fluid port 116. By contrast, FIG. 8B shows a female fluid port 116. FIG. 16 shows and describes one example of using the male and female fluid ports.

Generally, a technology-specific fluid port 116 can be provided in mixing-enhanced microfluidic container 110. That is, fluid port 116 (male or female) can be tailored to suit any collection and/or analysis technology. Examples of collection methods/devices include, but are not limited to, venipuncture, indwelling or central line (surgery), lancet (fingerstick), blood contacting equipment access (e.g., dialysis, extracorporeal membrane oxygenation (ECMO), apheresis), needleless devices (e.g., Hemolink, Tasso, Seventh Sense), intravenous (IV) line (e.g., Velano), and the like. Examples of analysis methods/devices include, but are not limited to, POC diagnostic cartridge (e.g., disposable cartridge), multi-well microplate (e.g., 48-well, 96-well), microfluidics system (MS), lab-on-a-chip (LOC) devices, pipetter (direct dispense), and the like.

Figure 9:
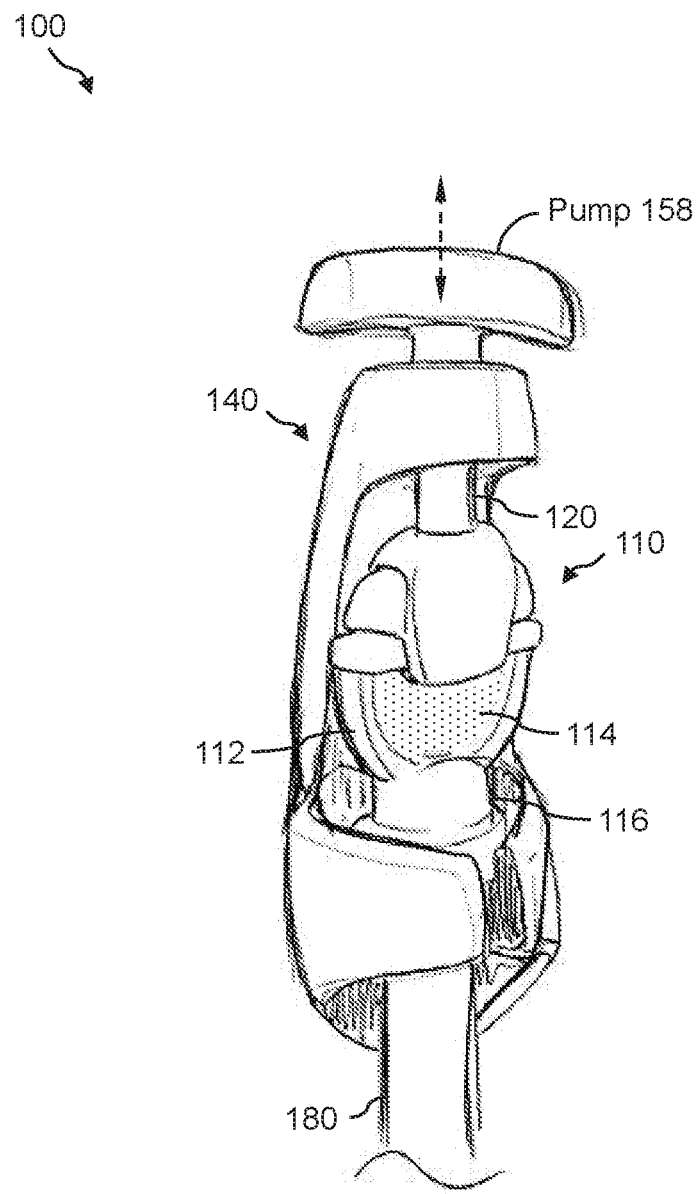
FIG. 9 illustrates a perspective view of the small volume sample collection system and an example of the pumping mechanism thereof.

FIG. 9 illustrates a perspective view of small volume sample collection system 100 and an example of the pumping mechanism thereof. In this example, pump 158 (see FIG. 7) is a manual syringe pump with a knob that can be pushed to provide positive pressure (for dispensing) and pulled to provide negative pressure (vacuum, for fluid draw) to reaction chamber 112 of mixing-enhanced microfluidic container 110.

Figure 10:
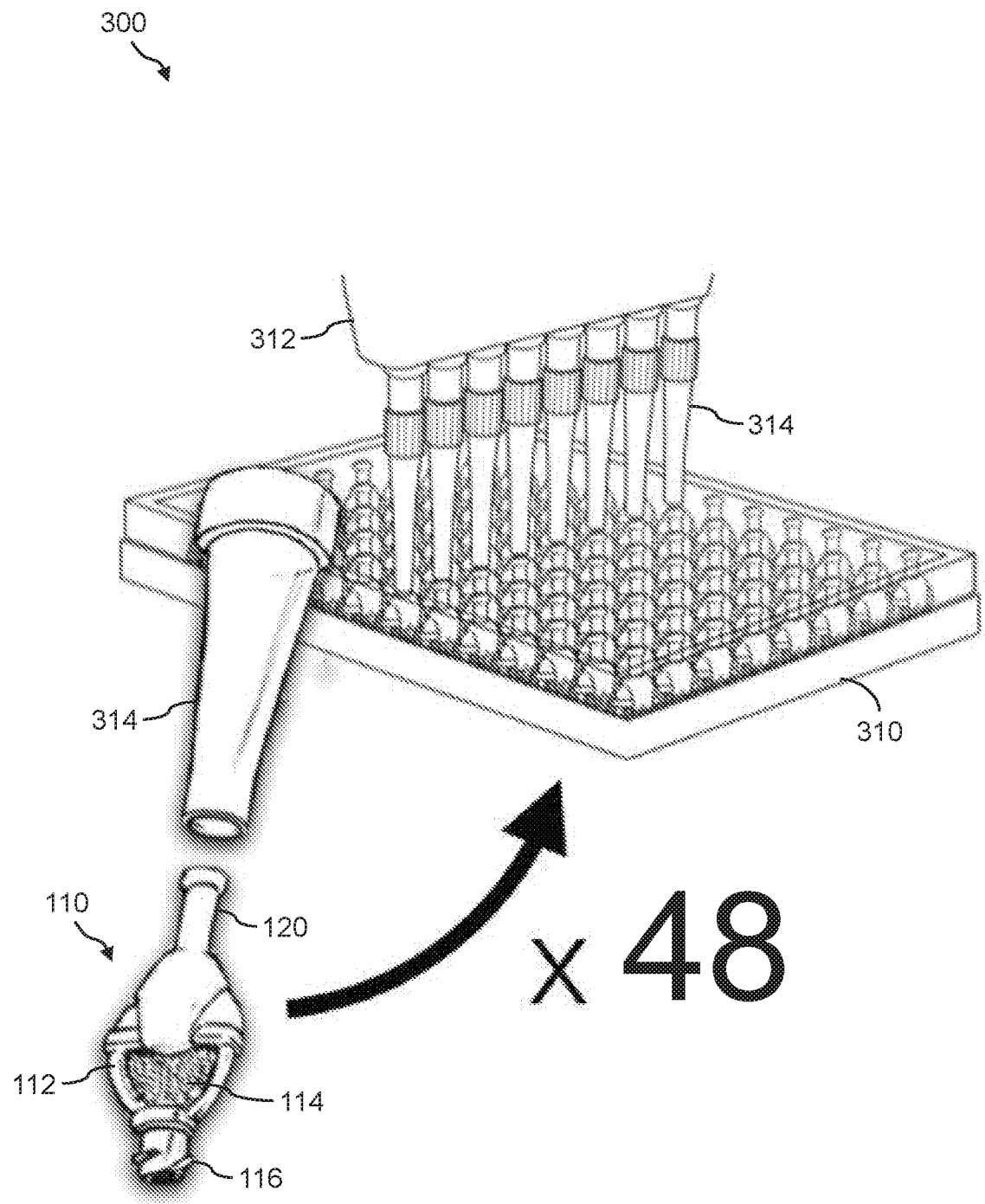
FIG. 10 illustrates a perspective view of a high-throughput sample processing system using the presently disclosed mixing-enhanced microfluidic container.
Figures 11A, 11B:
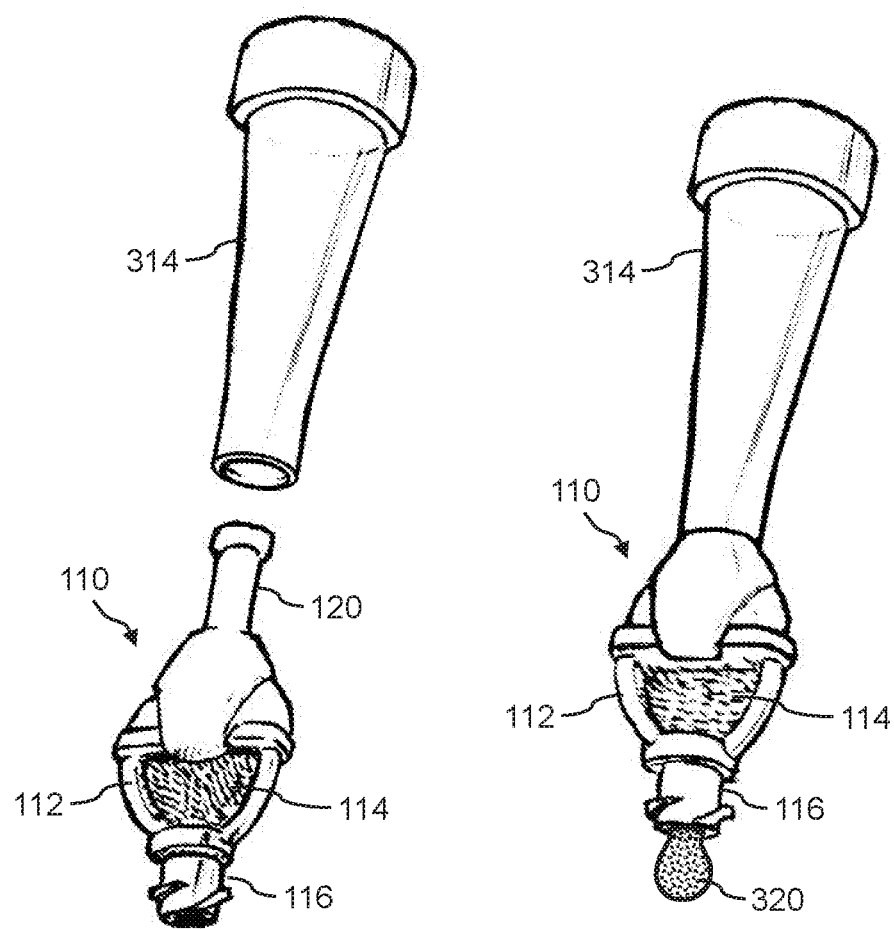
FIG. 11A and FIG. 11B illustrate perspective views of the mixing-enhanced microfluidic container in combination with a pipette adaptor for use in the high-throughput system.

FIG. 10 illustrates a perspective view of a high-throughput sample processing system 300 using the presently disclosed mixing-enhanced microfluidic container 110. High-throughput sample processing system 300 can be, for example, a high-throughput system used in a laboratory setting. High-throughput sample processing system 300 includes a multi-well microplate 310, such as a 48- or 96-well microplate and a robot 312 that is used to manipulate, for example, eight samples at one time. In this example, robot 312 includes a rack of eight pipette adaptor tips 314. Each of the pipette adaptor tips 314 is designed to receive cap 120 of mixing-enhanced microfluidic container 110 and apply positive pressure for dispensing sample fluid from the mixing-enhanced microfluidic container 110. FIG. 11A shows an example of pipette adaptor tip 314 aligning to cap 120 of mixing-enhanced microfluidic container 110, while FIG. 11B shows pipette adaptor tip 314 coupled to cap 120 of mixing-enhanced microfluidic container 110. FIG. 11B also shows positive pressure applied to mixing-enhanced microfluidic container 110, which causes sample fluid 320 to be dispensed from fluid port 116.

Figure 12:
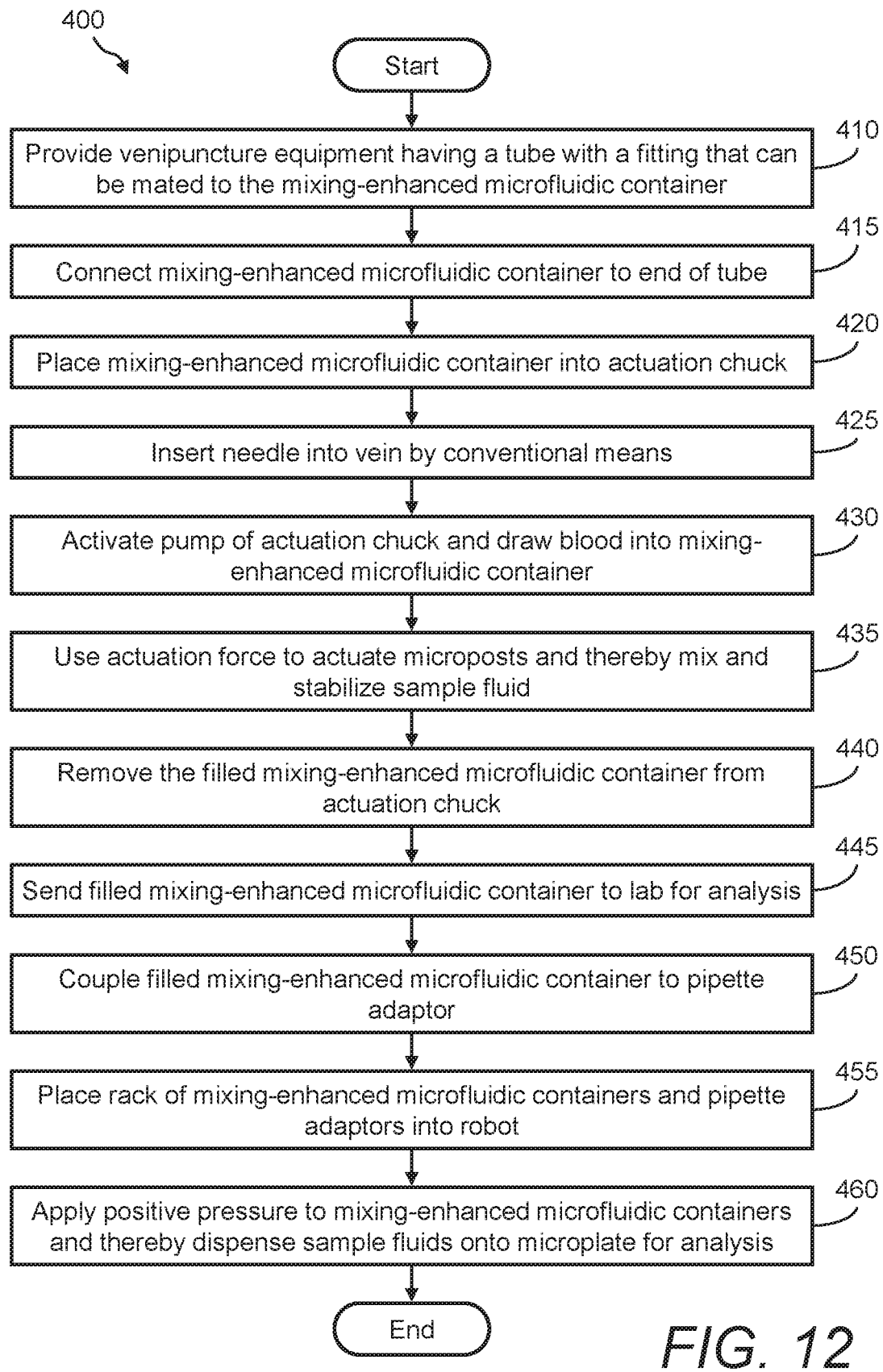
FIG. 12 illustrates a flow diagram of an example of a method of using the presently disclosed small volume sample collection system with an indwelling line in a high resource environment of blood collection and analysis.

FIG. 12 illustrates a flow diagram of an example of a method 400 of using the presently disclosed small volume sample collection system 100 with an indwelling line in a high resource environment of blood collection and analysis. Method 400 is an example of using the presently disclosed small volume sample collection system 100 in a high resource environment, such as a hospital setting, without drawing an excess of sample fluid, i.e., more than is needed. Method 400 may include, but is not limited to, the following steps.

At a step 410, venipuncture equipment is provided, wherein the venipuncture equipment has a tube (e.g., central line 180) with a fitting (e.g., fitting 182) that can be mated to the particular type of fluid port 116 of mixing-enhanced microfluidic container 110.

At a step 415, fluid port 116 of mixing-enhanced microfluidic container 110 is connected to the fitting (e.g., fitting 182) the end of the tube (e.g., central line 180) as shown, for example, in FIG. 2A.

At a step 420, mixing-enhanced microfluidic container 110 is placed into actuation chuck 140 as shown, for example, in FIG. 1 and FIG. 9.

At a step 425, a needle is inserted into the vein of the subject by conventional means.

At a step 430, pump 158 of actuation chuck 140 is activated and sample fluid (i.e., blood) is drawn into reaction chamber 112 of mixing-enhanced microfluidic container 110, an example of which is shown in FIG. 9. Then, mixing-enhanced microfluidic container 110 can be disconnected from the tube (e.g., central line 180).

At a step 435, actuation force 154 of actuation chuck 140 is used to actuate microposts 114 and thereby mix and stabilize the sample fluid (i.e., blood). For example, actuation mechanism 152 (e.g., motor 156 and magnets 150) is activated, which generates an actuation force 154 in proximity to microposts 114 that compels at least some of microposts 114 to exhibit motion. Microposts 114 are actuated for a long enough period of time to mix and stabilize the sample fluid (i.e., blood). In one example, UI 164 is used to activate actuation mechanism 152. In one example, upon activation, a green LED (an indicator 166) blinks while the actuation process is in progress and then turns on solid when actuation (i.e., mixing and stabilizing) is complete. In another example, upon activation, short beeping sounds (an indicator 166) are generated while the actuation process is in progress and then the beeps turn to a continuous sound when actuation (i.e., mixing and stabilizing) is complete.

At a step 440, the filled mixing-enhanced microfluidic container 110 is removed from actuation chuck 140.

At a step 445, an identification means (e.g., barcode) is placed on mixing-enhanced microfluidic container 110. Then, the filled mixing-enhanced microfluidic container 110 is sent to a laboratory for analysis.

At a step 450, at the laboratory, which is using a high-throughput system, such as high-throughput sample processing system 300 shown in FIG. 10, cap 120 of the filled mixing-enhanced microfluidic container 110 is coupled to the tip of pipette adaptor 314.

At a step 455, a rack (e.g., 8-well rack) of mixing-enhanced microfluidic containers 100 and pipette adaptors 314 is placed into the robot, such as robot 312 shown in FIG. 10.

At a step 460, using pipette adaptors 314 of robot 312, positive pressure is applied to the reaction chambers 112 of mixing-enhanced microfluidic containers 100, thereby dispensing sample fluids onto multi-well microplate 310 for analysis. FIG. 11B shows an example of using pipette adaptor 314 to apply positive pressure to mixing-enhanced microfluidic container 110 and dispense sample fluid 320 from fluid port 116.

Figure 13:
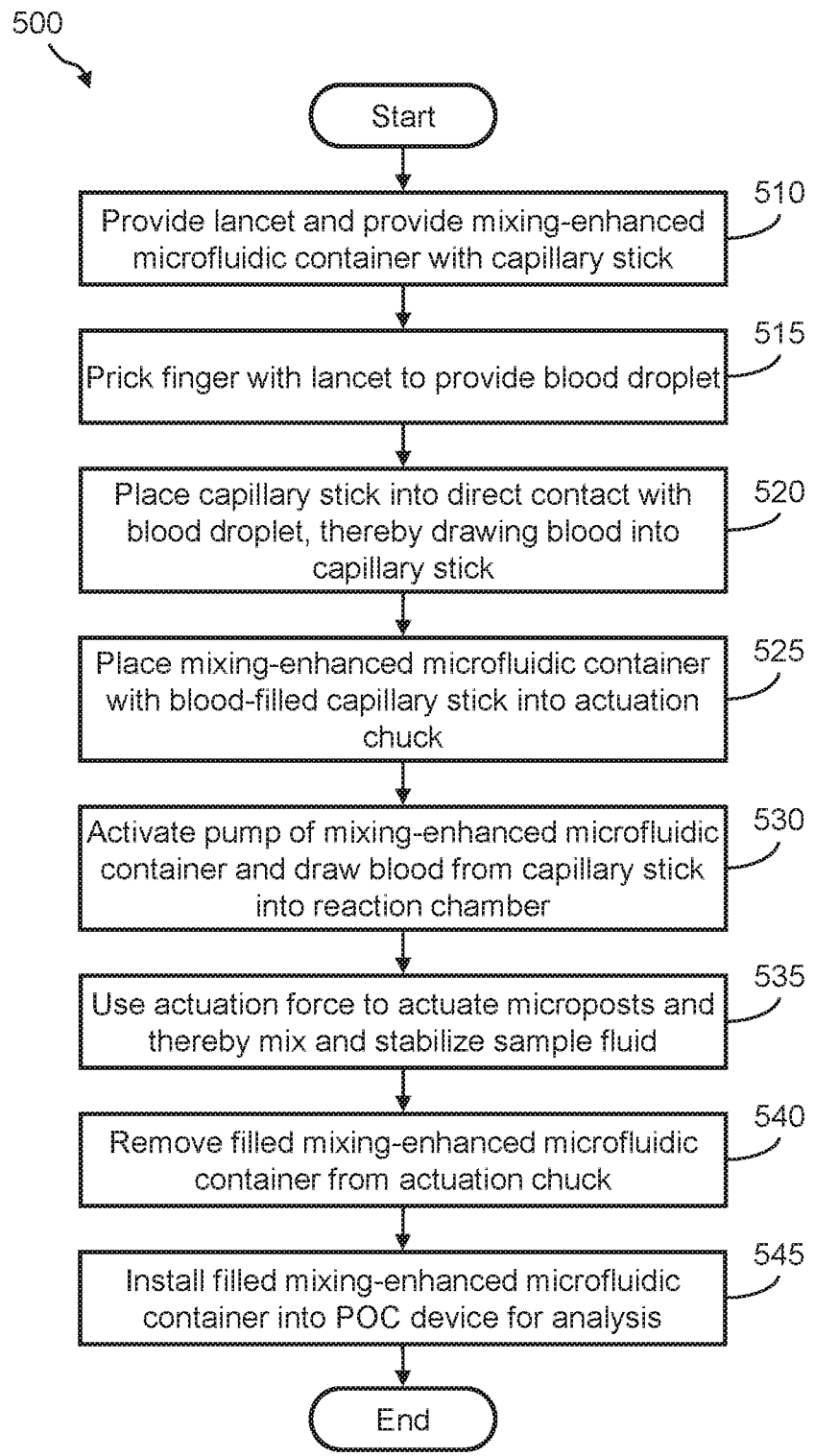
FIG. 13, FIG. 14, and FIG. 15 show an example of a process of using the presently disclosed small volume sample collection system in a low resource environment of blood collection and analysis.
Figure 14:
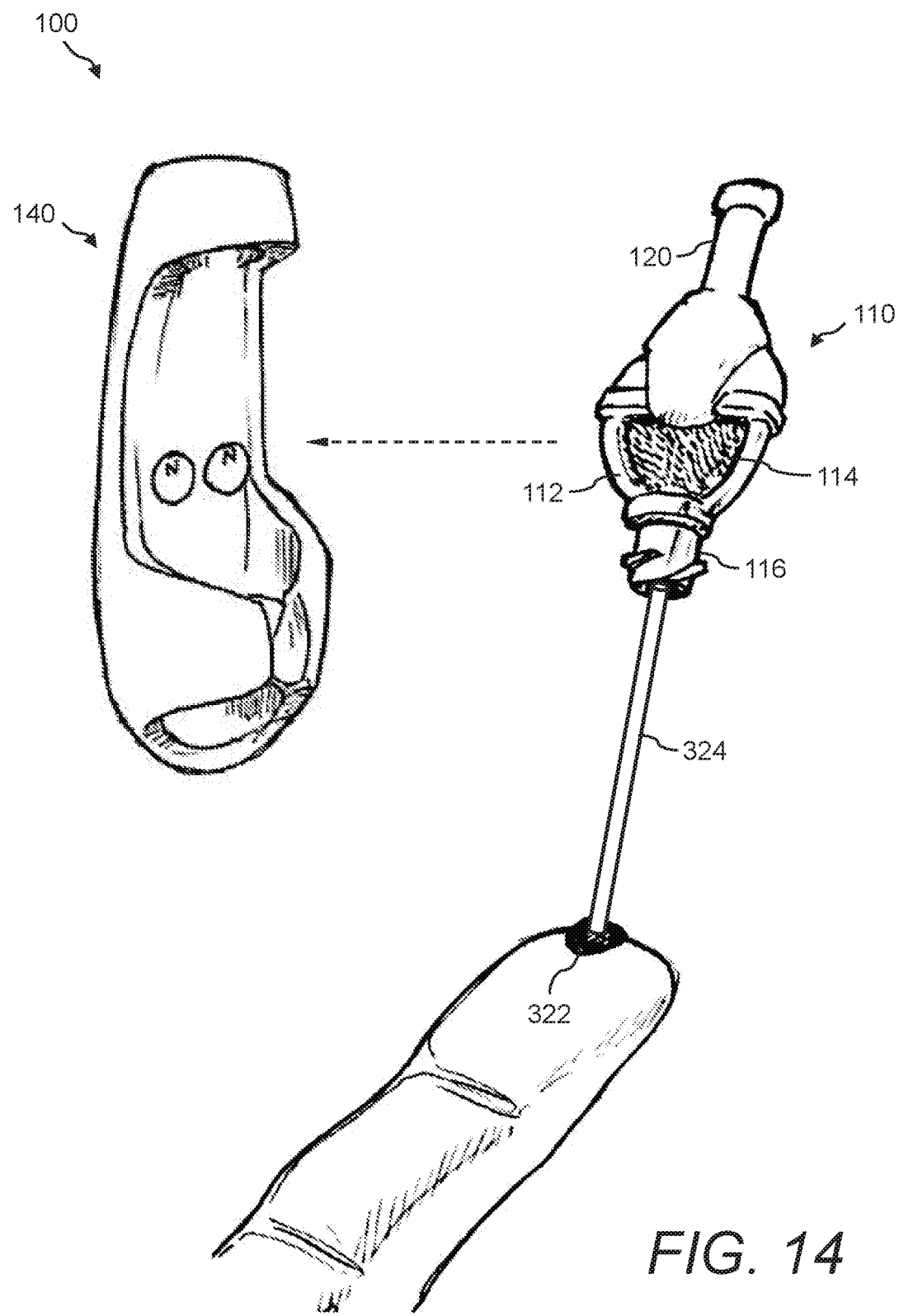
Figure 15:
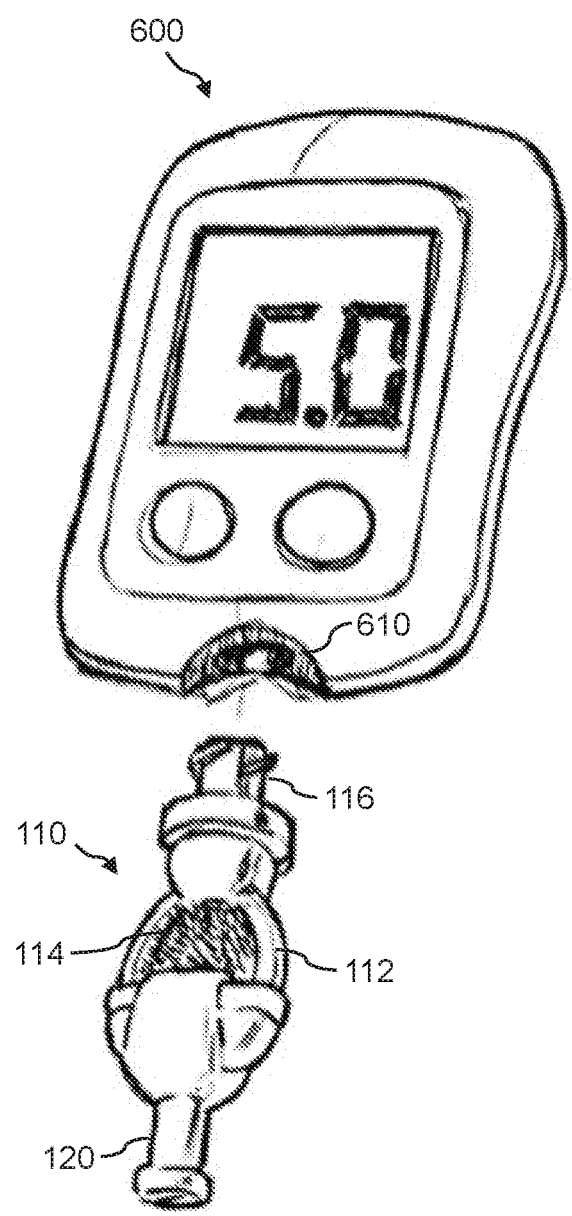

FIG. 13, FIG. 14, and FIG. 15 show an example of a process of using the presently disclosed small volume sample collection system 100 in a low resource environment of blood collection and analysis. Namely, FIG. 13 illustrates a flow diagram of an example of a method 500 of using the presently disclosed small volume sample collection system 100 with a POC device in a low resource environment of blood collection and analysis. Method 500 is an example of using the presently disclosed small volume sample collection system 100 in a low resource environment, such as a POC setting, while providing the ability to properly mix and stabilize a small volume of sample fluid, such as blood. Method 500 may include, but is not limited to, the following steps.

At a step 510, a lancet is provided and mixing-enhanced microfluidic container 110 is provided along with a capillary stick. For example and referring now to FIG. 14, a capillary stick 324 is coupled to fluid port 116 of mixing-enhanced microfluidic container 110.

At a step 515, a finger is pricked with the lancet to provide a blood droplet. For example, FIG. 14 shows a blood sample 322 that is the result of a fingerstick with a lancet.

At a step 520, the capillary stick is placed into direct contact with the blood droplet, thereby drawing blood into the capillary stick. For example, FIG. 14 shows the distal end of capillary stick 324 is placed into direct contact with blood sample 322, thereby drawing a small volume of blood sample 322 into capillary stick 324.

At a step 525, mixing-enhanced microfluidic container 110 with the blood-filled capillary stick 324 still coupled thereto is placed into actuation chuck 140, again see FIG. 14.

At a step 530, pump 158 (see FIG. 9) of actuation chuck 140 is activated and blood sample 322 is drawn from capillary stick 324 into reaction chamber 112 of mixing-enhanced microfluidic container 110. Then, capillary stick 324 can be disconnected from mixing-enhanced microfluidic container 110.

At a step 535, actuation force 154 of actuation chuck 140 is used to actuate microposts 114 and thereby mix and stabilize blood sample 322. For example, actuation mechanism 152 (e.g., motor 156 and magnets 150) is activated, which generates an actuation force 154 in proximity to microposts 114 that compels at least some of microposts 114 to exhibit motion. Microposts 114 are actuated for a long enough period of time to mix and stabilize blood sample 322. In one example, UI 164 is used to activate actuation mechanism 152. In one example, upon activation, a green LED (an indicator 166) blinks while the actuation process is in progress and then turns on solid when actuation (i.e., mixing and stabilizing) is complete. In another example, upon activation, short beeping sounds (an indicator 166) are generated while the actuation process is in progress and then the beeps turn to a continuous sound when actuation (i.e., mixing and stabilizing) is complete.

At a step 540, the filled mixing-enhanced microfluidic container 110 is removed from actuation chuck 140.

At a step 545, the filled mixing-enhanced microfluidic container 110 is installed into a POC device for analysis. For example and referring now to FIG. 15, the filled mixing-enhanced microfluidic container 110 is placed into a POC device, such as POC device 600 that has an input port 610, for analysis. In another example, the filled mixing-enhanced microfluidic container 110 can be shipped to a laboratory for analysis.

FIG. 16 illustrates an example of a configuration that includes a "collection" mixing-enhanced microfluidic container 110 supplying an "analysis" mixing-enhanced microfluidic container 110. A first mixing-enhanced microfluidic container 110 (e.g., 110A) is configured for sample fluid collection and is holding the collected sample fluid. However, mixing-enhanced microfluidic container 110A may not be configured for on-device analysis. For example, mixing-enhanced microfluidic container 110A may include a certain type of anticoagulant and/or blood stabilization reagent. Accordingly, a second mixing-enhanced microfluidic container 110 (e.g., 110B) is provided that is configured for sample fluid analysis. For example, mixing-enhanced microfluidic container 110B may include a certain type of analytic reagent. In this example, mixing-enhanced microfluidic container 110A has a threaded male type of fluid port 116 and mixing-enhanced microfluidic container 110B has a threaded (not visible) female type of fluid port 116.

In operation, the male-type fluid port 116 of mixing-enhanced microfluidic container 110A is mechanically and fluidly coupled to the female-type fluid port 116 of mixing-enhanced microfluidic container 110B. Then, once mated together, one of three scenarios can occur (1) mixing-enhanced microfluidic container 110A (the collection device) is installed into actuation chuck 140 and positive pressure is applied to mixing-enhanced microfluidic container 110A to push the sample fluid out of reaction chamber 112 of mixing-enhanced microfluidic container 110A and into reaction chamber 112 of mixing-enhanced microfluidic container 110B (the analysis device), (2) mixing-enhanced microfluidic container 110B is installed into actuation chuck 140 and negative pressure is applied to mixing-enhanced microfluidic container 110B (and also negative pressure transfers to 110A) to draw the sample fluid out of reaction chamber 112 of mixing-enhanced microfluidic container 110A (the collection device) and into reaction chamber 112 of mixing-enhanced microfluidic container 110B (the analysis device), or (3) mixing-enhanced microfluidic container 110A is installed into actuation chuck 140 and mixing-enhanced microfluidic container 110B is also installed into actuation chuck 140. Then, positive pressure is applied to mixing-enhanced microfluidic container 110A (the collection device) and negative pressure is applied to mixing-enhanced microfluidic container 110B (the analysis device), which causes the sample fluid to flow out of reaction chamber 112 of mixing-enhanced microfluidic container 110A and into reaction chamber 112 of mixing-enhanced microfluidic container 110B.

Figure 17:
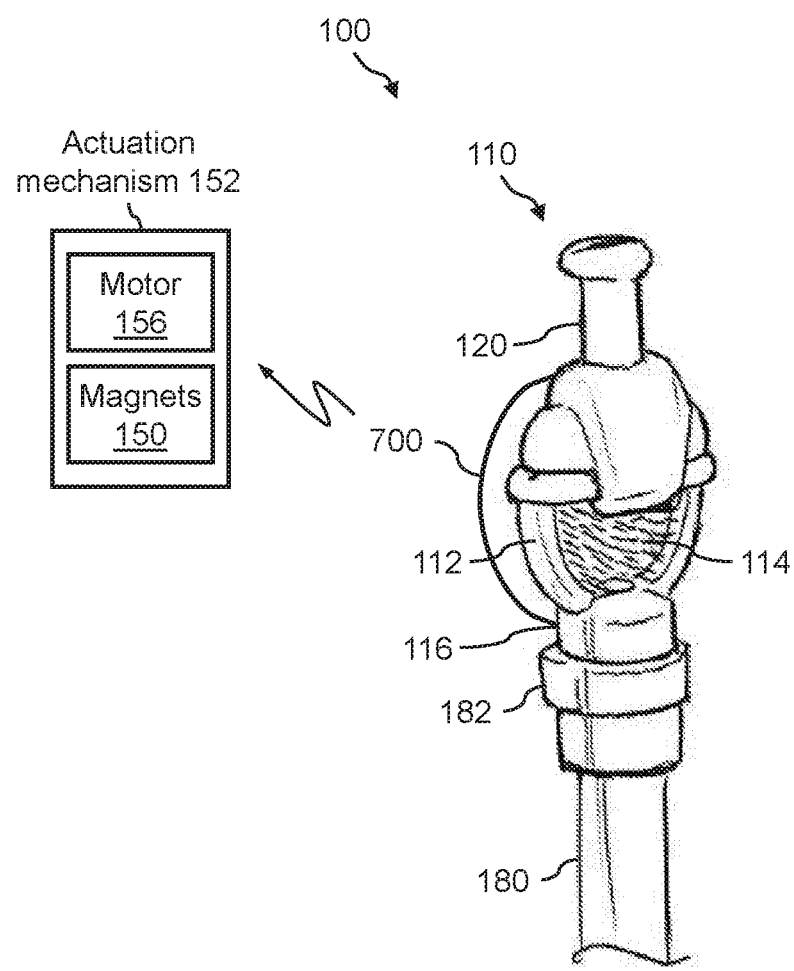
FIG. 17 illustrates a perspective view of an example of the presently disclosed small volume sample collection system that includes a mixing-enhanced microfluidic container with an integrated actuation mechanism.

FIG. 17 illustrates a perspective view of an example of the presently disclosed small volume sample collection system 100 that includes mixing-enhanced microfluidic container 110 with an integrated actuation mechanism. For example, FIG. 17 shows an actuation subsystem 700 integrated directly to the reaction chamber 112-portion of the mixing-enhanced microfluidic container 110. Actuation subsystem 700 can be any mechanism that generates an actuation force with respect to microposts 114, wherein the actuation force may be, for example, magnetic, thermal, sonic, optical, electrical, and/or vibrational. In one example, actuation subsystem 700 can be the actuation mechanism 152 described in FIG. 7 that includes the motor 156 and magnets 150. In some embodiments, the mixing-enhanced microfluidic container is integrated with the actuation mechanism via a printed circuit board, a thin film magnetic circuit, or wires embedded in the microposts.

In the embodiment of small volume sample collection system 100 shown in FIG. 17, instead of the mixing-enhanced microfluidic container 110 and the reusable actuation chuck 140 being provided separately, the actuation mechanism (e.g., actuation subsystem 700) is integrated together with mixing-enhanced microfluidic container 110. In so doing, the actuation mechanism (e.g., actuation subsystem 700) replaces the reusable actuation chuck 140. Further, the actuation mechanism (e.g., actuation subsystem 700) can be disposable along with the mixing-enhanced microfluidic container 110.

In a further embodiment that is particularly useful in low resource environments, in either the reusable actuation chuck or the integrated magnet configuration, the actuator is a permanent magnet configured such that shaking the device causes the magnet and therefore the microposts to move.

In summary and referring now to FIG. 1 through FIG. 17, the presently disclosed small volume sample collection system 100 that includes mixing-enhanced microfluidic container 110 and actuation chuck 140 is useful in both the high and low resource environments of blood collection and analysis. Namely, mixing-enhanced microfluidic container 110 is useful for both collection and analysis and can be integrated with any types of existing collection and analysis infrastructure. Further, mixing-enhanced microfluidic container 110 of small volume sample collection system 100 provides enhanced mixing in a capillary draw device that is not currently possible in, for example, POC low resource environments. Additionally, mixing-enhanced microfluidic container 110 of small volume sample collection system 100 can be configured for sample fluid collection, sample fluid analysis, or both sample fluid collection and analysis.

What is claimed is:

1. A small volume sample collection system comprising:
a mixing-enhanced microfluidic container configured to collect a sample comprising a volume of biological fluid of less than about 0.1 ml; and
a reusable actuation chuck;
wherein the mixing-enhanced microfluidic container comprises a reaction chamber, wherein the reaction chamber further comprises reagents disposed within the reaction chamber and mixing means configured to mix the biological fluid with the reagents, and
wherein the mixing means comprise an array of surface attached posts configured for actuation in the presence of an actuation force.

2. The small volume sample collection system of claim 1, wherein the reusable actuation chuck is configured to provide the actuation force when the mixing-enhanced microfluidic container is contacted with the reusable actuation chuck.

3. The small volume sample collection system of claim 1, wherein the mixing-enhanced microfluidic container is installed within the reusable actuation chuck.

4. The small volume sample collection system of claim 1, wherein the actuation force is selected from the group consisting of a magnetic field, a thermal field, a sonic field, an optical field, an electrical field, and a vibrational field.

5. The small volume sample collection system of claim 1, wherein the reagents disposed within the reaction chamber are disposed on or integrated with an inside surface of the reaction chamber.

6. The small volume sample collection system of claim 1, wherein the reagents disposed within the reaction chamber are disposed on or integrated with an outer surface of at least some of the surface-attached posts.

7. The small volume sample collection system of claim 1, wherein the biological fluid is selected from the group consisting of blood, urine, saliva, sputum, mucus, feces, tumor fluid, needle biopsy fluid, peritoneal fluid, cerebral spinal fluid, tears, sweat, synovial fluid, semen, ear fluid, breast milk, and bile.

8. The small volume sample collection system of claim 7, wherein the biological fluid is blood, and wherein the mixing-enhanced microfluidic container is configured to collect blood samples produced via lancet or via central line.

9. The small volume sample collection system of claim 7, wherein the mixing-enhanced microfluidic container is configured to connect to a point-of-care (POC) diagnostic device.

10. The small volume sample collection system of claim 7, wherein the mixing-enhanced microfluidic container is configured to connect to a dispensing pipette.

11. The small volume sample collection system of claim 10, further comprising a plurality of mixing-enhanced microfluidic containers and reusable actuation chucks, and wherein the plurality of mixing-enhanced microfluidic containers are configured to connect to a plurality of dispensing pipettes configured in an array for high-throughput sample processing.

12. The small volume sample collection system of claim 1, wherein the reaction chamber is configured to hold from about 5 uL to about 500 uL of biological fluid.

13. The small volume sample collection system of claim 12, wherein the reaction chamber is configured to hold about 50 uL of biological fluid.

14. The small volume sample collection system of claim 1, wherein a fluid port supplies one end of the reaction chamber and a vent mechanism is provided at the other end of the reaction chamber.

15. The small volume sample collection system of claim 14, wherein a central line is mechanically and fluidly coupled to the fluid port.

16. The small volume sample collection system of claim 15, wherein a cap is mechanically coupled to the vent mechanism.

17. The small volume sample collection system of claim 15, wherein the reusable actuation chuck comprises a housing, and wherein the housing comprises a wraparound portion for receiving the fluid port of the reaction chamber.

18. The small volume sample collection system of claim 17, wherein the wraparound portion comprises a slot configured to allow the central line to pass through the slot.

19. The small volume sample collection system of claim 18, wherein the housing comprises a cap portion and a holding portion, wherein the cap portion is configured to engage with a cap end of the mixing-enhanced microfluidic container, and wherein the holding portion is arranged between the wraparound portion and the cap portion of the housing.

20. The small volume sample collection system of claim 19, wherein the holding portion is configured to hold the reaction chamber.

21. The small volume sample collection system of claim 1, wherein the actuation chuck further comprises one or more components selected from the group consisting of a battery, a motor, one or more magnets, a pump, a controller, one or more visual, audible, and/or tactile indicators, and a communications interface.

\* \* \* \* \*